(12) United States Patent
Narula et al.

(10) Patent No.: US 7,446,080 B2
(45) Date of Patent: Nov. 4, 2008

(54) COMPOUNDS 6-OXABICYLCO[3.2.1]OCTANE, 5-METHYL-1-(1,2,2-TRIMETHYLBICYCLO[3.1.0]HEX-3-YL)-, 2-OXABICYCLO[2,2,2]OCTANE, 1-METHYL-4-(1,2,2-TRIMETHYLBICYCLO [3,1,0]HEX-3-YL)-, AND THEIR USES IN FRAGRANCE APPLICATIONS

(75) Inventors: Anubhav P. S. Narula, Monmouth, NJ (US); Edward Mark Arruda, Easton, PA (US)

(73) Assignee: International Flavors & Fragrances Inc., New York, NY (US)

( * ) Notice: Subject to any disclaimer, the term of this patent is extended or adjusted under 35 U.S.C. 154(b) by 0 days.

(21) Appl. No.: 11/947,218

(22) Filed: Nov. 29, 2007

(65) Prior Publication Data

US 2008/0139447 A1    Jun. 12, 2008

Related U.S. Application Data

(63) Continuation-in-part of application No. 11/608,487, filed on Dec. 8, 2006.

(51) Int. Cl.
*C11D 3/50* (2006.01)

(52) U.S. Cl. .................... 510/103; 510/104; 512/11; 512/14; 549/386

(58) Field of Classification Search ............. 510/103, 510/104; 512/11, 14; 549/386
See application file for complete search history.

(56) References Cited

U.S. PATENT DOCUMENTS 5,081,262 A    1/1992  Narula et al.
2008/0139448 A1*  6/2008  Narula et al. ............. 512/13

OTHER PUBLICATIONS

Ashby, E.C. et al. "The Mechanism of Reaction of Geminal Dihalides with Sodium Trimethyltin. Evidence for a Single Electron Transfer Initiated Reaction Which Produces Both Radical and Carbene Intermediates" J. Org. Chem. Dec. 1994 59(24) pp. 7358-7366.
Ashby, E.C. et al. "Electron Transfer in the Reactions of Geminal Dihalides with Ph2P-Evidence for the Formation of a Carbene Intermediate from a Radical Precursor" J. Org. Chem. Nov. 1995 60(22) pp. 7117-7124.
Material Safety Data Sheet for Cassifix, Ventos Essential Oils, Barcelona, Spain May 2003.

* cited by examiner

*Primary Examiner*—John R Hardee
(74) *Attorney, Agent, or Firm*—Elizabeth M. Quirk; XuFan Tseng

(57) ABSTRACT

The compounds 6-oxabicylco[3.2.1]octane, 5-methyl-1-(1,2, 2-trimethylbicyclo [3.1.0]hex-3-yl)- and 2-oxabicyclo[2,2,2] octane, 1-methyl-4-(1,2,2-trimethylbicyclo [3,1,0]hex-3yl)-, and their uses in fragrance applications.

3 Claims, No Drawings

COMPOUNDS 6-OXABICYLCO[3.2.1]OCTANE, 5-METHYL-1-(1,2,2-TRIMETHYLBICYCLO[3.1.0]HEX-3-YL)-, 2-OXABICYCLO[2,2,2]OCTANE, 1-METHYL-4-(1,2,2-TRIMETHYLBICYCLO[3,1,0]HEX-3-YL)-, AND THEIR USES IN FRAGRANCE APPLICATIONS

STATUS OF RELATED APPLICATIONS

This application is a continuation-in-part of U.S. Ser. No. 11/608,487, now allowed, filed on Dec. 8, 2006, the contents hereby incorporated by reference as if set forth in its entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow perfumers to apply the new compounds in creating new fragrances.

SUMMARY OF THE INVENTION

The present invention provides novel chemicals, and the use of the chemicals to enhance the fragrance of perfumes, toilet waters, colognes, personal products and the like. In addition, the present invention is directed to the use of the novel chemicals to enhance fragrance in perfumes, toilet waters, colognes, personal products and the like.

More specifically, the invention relates to a novel composition comprising compounds 6-oxabicylco[3.2.1]octane, 5-methyl-1-(1,2,2-trimethylbicyclo[3.1.0]hex-3-yl)- and 2-oxabicyclo [2,2,2]octane, 1-methyl-4-(1,2,2-trimethylbicyclo[3,1,0]hex-3-yl)- represented by structures 1 and 2, respectively:

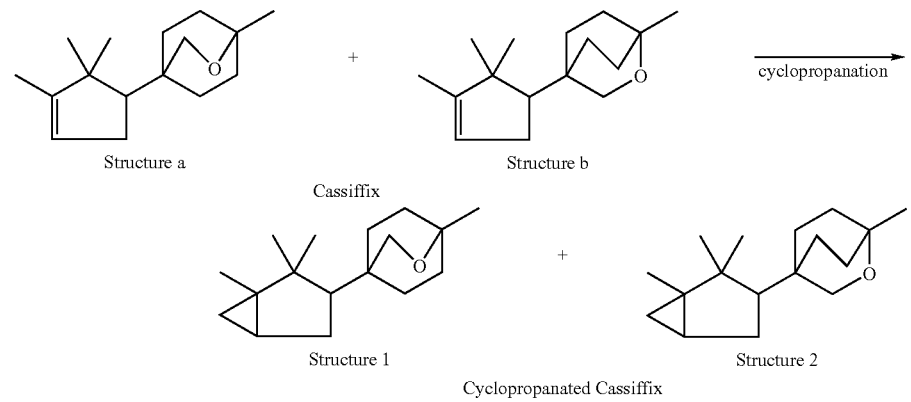

Structure 1

Structure 2

DETAILED DESCRIPTION OF THE INVENTION

According to the present invention, 6-oxabicylco[3.2.1]octane, 5-methyl-1-(1,2,2-trimethylbicyclo[3.1.0]hex-3-yl)- and 2-oxabicyclo[2,2,2]octane, 1-methyl-4-(1,2,2-trimethylbicyclo[3,1,0]hex-3-yl)- may be made by any convenient method, an especially preferred method being the cyclopropanation of a suitable substituted alkene, comprising the reaction of the alkene with a carbenoide, generated from diiodomethane and a Zn—Cu compound.

Cassiffix contains, as known by one skilled in the art, 2-oxa-bicyclo[2.2.2]octane, 1-methyl-4-(2,2,3-trimethyl-cyclopent-3-enyl)- (shown as "Structure a" in the above scheme) and 2-oxa-bicyclo[2.2.2]octane, 1-methyl-4-(2,2,3-trimethyl-cyclopent-3-enyl)- (shown as "Structure b" in the above scheme). Cyclopropanation of Cassiffix provides compounds of the present invention 6-oxabicylco[3.2.1]octane, 5-methyl-1-(1,2,2-trimethylbicyclo[3.1.0]hex-3-yl)- and 2-oxabicyclo[2,2,2]octane, 1-methyl-4-(1,2,2-trimethylbicyclo[3,1,0]hex-3-yl)-.

We have discovered a novel composition comprising 6-oxabicylco[3.2.1]octane, 5-methyl-1-(1,2,2-trimethylbicyclo[3.1.0]hex-3-yl)- and 2-oxabicyclo[2,2,2]octane, 1-methyl-4-(1,2,2-trimethylbicyclo[3,1,0]hex-3-yl)-.

These compounds are useful as ingredients in fragrance applications. The invention therefore also provides the use in a fragrance application the composition of 6-oxabicylco [3.2.1]octane, 5-methyl-1-(1,2,2-trimethylbicyclo[3.1.0] hex-3-yl)- and 2-oxabicyclo [2,2,2]octane, 1-methyl-4-(1,2,2-trimethylbicyclo[3,1,0]hex-3-yl)-.

The compounds have smooth, ambery, floral, eucalyptus, green buds and cassis fragrance notes.

The use of the compounds of the present invention is widely applicable in current perfumery products, including the preparation of perfumes and colognes, the perfuming of personal care products such as soaps, shower gels, and hair care products as well as air fresheners and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory effective amount is understood to mean the amount of compound in perfume compositions the individual component will contribute to its particular olfactory characteristics, but the olfactory effect of the perfume composition will be the sum of the effects of each of the perfumes or fragrance ingredients. Thus the compounds of the invention can be used to alter the aroma characteristics of the perfume composition, or by modifying the olfactory reaction contributed by another ingredient in the composition. The amount will vary depending on many factors including other ingredients, their relative amounts and the effect that is desired.

The level of compound of the invention employed in the perfumed article varies from about 0.005 to about 10 weight percent, preferably from about 0.5 to about 8 and most preferably from about 1 to about 7 weight percent. In addition to the compounds other agents can be used in conjunction with the fragrance. Well known materials such as surfactants, emulsifiers, polymers to encapsulate the fragrance can also be employed without departing from the scope of the present invention.

Another method of reporting the level of the compounds of the invention in the perfumed composition, i.e., the compounds as a weight percentage of the materials added to impart the desired fragrance. The compounds of the invention can range widely from 0.005 to about 70 weight percent of the perfumed composition, preferably from about 0.1 to about 50 and most preferably from about 0.2 to about 25 weight percent. Those with skill in the art will be able to employ the desired level of the compounds of the invention to provide the desired fragrance and intensity.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million and g is understood to be grams. All U.S. patents mentioned above are incorporated herein by reference. IFF as used in the examples is understood to mean International Flavors & Fragrances Inc., New York, N.Y., USA. All fragrance materials mentioned in the examples are available from IFF.

EXAMPLE I

PREPARATION OF
2-OXABICYCLO[2,2,2]OCTANE, 1-METHYL-
4-(1,2,2-TRIMETHYLBICYCLO[3,1,0]HEX-3YL)-

To a dry 200 ml multi-neck round bottom flask fitted with an air stirrer, nitrogen inlet condenser and an addition funnel 23.4 g of Cassifix®, 13 g of ZnCu, 54 g $CH_2I_2$ and 100 g $Et_2O$ were charged to the flask and stirred. The mixture was heated to reflux and maintained and then the reaction mixture was cooled and quenched with 50 mL of $NH_4$ CL aqueous solution. The contents were transferred into a separatory funnel and aqueous layer was separated. The organic layer was dried over anhydrous sodium sulfate and then concentrated to give the crude product containing both 6-oxabicylco[3.2.1]octane, 5-methyl-1-(1,2,2-trimethylbicyclo[3.1.0]hex-3-yl)- and 2-oxabicyclo[2,2,2]octane, 1-methyl-4-(1,2,2-trimethylbicyclo[3,1,0]hex-3-yl)-. 2-Oxabicyclo [2,2,2]octane, 1-methyl-4-(1,2,2-trimethylbicyclo[3,1,0]hex-3-yl)- was then isolated from the crude product using capillary GLC trapping and identified.

The compound has smooth, ambery, floral, eucalyptus, green buds and cassis fragrance notes.

The NMR spectrum of 2-oxabicyclo[2,2,2]octane, 1-methyl-4-(1,2,2-trimethylbicyclo[3,1,0]hex-3-yl)- is as follows: 0.4 ppm (s, 1H); 0.8 ppm (s, 1H); 0.9-1.0 ppm (m, 10H); 1.5 ppm (s, H); 1.6-1.8 ppm (m, 8H).

EXAMPLE II

DEMONSTRATION FORMULA CONTAINING
THE COMPOSITION OF 6-OXABICYLCO[3.2.1]
OCTANE, 5-METHYL-1-(1,2,2-TRIMETHYLBI-
CYCLO[3.1.0]HEX-3-YL)- AND 2-OXABICYCLO
[2,2,2]OCTANE, 1-METHYL-4-(1,2,2-
TRIMETHYLBICYCLO [3,1,0]HEX-3YL)-
("THE COMPOSITION")

| Fragrance Ingredient | Weight (g) |
| --- | --- |
| THE COMPOSITION | 10.00 |
| DIPROPYLENE GLYCOL (DPG) | 0.00 |
| ALLYL AMYL GLYCOLATE | 5.00 |
| AMYL SALICYLATE | 30.00 |
| BACDANOL | 20.00 |
| CALONE CAM 10% DPG | 5.00 |
| CEDRAMBER | 30.00 |
| CYCLAMAL EXTRA | 3.00 |
| DIHYDRO MYRCENOL | 115.00 |
| DYNASCONE 10 | 10.00 |
| FLORALOZONE | 1.00 |
| FLORIFFONE TD DIHYDRO 10% DPG | 15.00 |

-continued

| Fragrance Ingredient | Weight (g) |
|---|---|
| GALAXOLIDE 50 | 145.00 |
| GERANIUM AFRICAN | 2.00 |
| HEDIONE | 70.00 |
| HELIONAL | 60.00 |
| ISO BUTYL QUINOLINE | 0.40 |
| ISO E SUPER | 100.00 |
| ORANGE OIL FLA CP | 15.00 |
| PRECYCLEMONE B | 5.00 |
| THYME OIL WHITE 10% DPG | 6.00 |
| TRIPLAL | 7.00 |
| VERAMOSS | 5.00 |
| VERTOFIX COEUR | 20.00 |
| Total | 679.40 |

The composition of 6-oxabicylco[3.2.1]octane, 5-methyl-1-(1,2,2-trimethylbicyclo[3.1.0]hex-3-yl)- and 2-oxabicyclo[2,2,2]octane, 1-methyl-4-(1,2,2-trimethylbicyclo[3,1,0]hex-3-yl)- has smooth, ambery, floral, eucalyptus, green buds and cassis fragrance notes.

What is claimed is:

1. A composition comprising 6-oxabicylco[3.2.1]octane, 5-methyl-1-(1,2,2-trimethylbicyclo [3.1.0]hex-3-yl)- and 2-oxabicyclo[2,2,2]octane, 1-methyl-4-(1,2,2-trimethylbicyclo [3,1,0]hex-3-yl)-.

2. A method of improving, enhancing or modifying a fragrance formulation through the addition of an olfactory acceptable amount of the composition of claim 1.

3. A fragrance formulation containing an olfactory effective amount of the composition of claim 1.

* * * * *